United States Patent
Carr

[11] Patent Number: 5,537,203
[45] Date of Patent: Jul. 16, 1996

[54] INTEGRATED SPHERE FOR DIFFUSAL REFLECTANCE AND TRANSMITTANCE

[75] Inventor: Kevin F. Carr, Sunapee, N.H.

[73] Assignee: Labsphere, Inc., North Sutton, N.H.

[21] Appl. No.: 197,651

[22] Filed: Feb. 16, 1994

Related U.S. Application Data

[63] Continuation of Ser. No. 924,401, Aug. 4, 1992, abandoned, which is a continuation of Ser. No. 693,340, Apr. 29, 1991, abandoned.

[51] Int. Cl.$^6$ ........................................ G01J 1/04
[52] U.S. Cl. .................. 356/236; 356/446; 356/244; 356/440; 250/228
[58] Field of Search ........................... 356/236, 445, 356/446, 402, 432, 436, 437, 440, 319, 326, 244, 246; 250/228, 574

[56] References Cited

U.S. PATENT DOCUMENTS

| | | | |
|---|---|---|---|
| 3,545,871 | 12/1970 | Waska | 356/236 |
| 3,764,364 | 10/1973 | Seiner | 117/18 |
| 3,956,201 | 5/1976 | Seiner | 356/236 |
| 4,035,085 | 7/1977 | Seiner | 356/179 |
| 4,583,860 | 4/1986 | Butner | 356/236 |
| 4,645,922 | 2/1987 | Welbourn et al. | 356/236 |
| 4,838,688 | 6/1989 | Rhoads | 356/236 |
| 4,912,720 | 3/1990 | Springsteen | 372/72 |
| 4,995,727 | 2/1991 | Kawagoe et al. | 356/236 |

FOREIGN PATENT DOCUMENTS

| | | | |
|---|---|---|---|
| 0305224 | 12/1988 | Japan | 356/236 |
| 0305221 | 12/1988 | Japan | 356/236 |

*Primary Examiner*—Hoa Q. Pham
*Attorney, Agent, or Firm*—Rines and Rines

[57] ABSTRACT

A novel light integrating sphere of a preferably appropriately sintered fluorinated aliphatic long chain addition solid polymer block, hollowed to provide an internal integral diffuse reflectance spherical surface.

5 Claims, 2 Drawing Sheets

INTEGRATED SPHERE FOR DIFFUSAL REFLECTANCE AND TRANSMITTANCE

This application is a file wrapper continuation of application Ser. No. 924,401, filed Aug. 4, 1992, now abandoned, in turn a continuation of parent application Ser. No. 693,340 filed Apr. 29, 1991 now abandoned.

The present invention relates to spectrophotometric measurement apparatus and the like, being more specifically directed to integrating sphere accessories for such spectrophotometers, colorimeters, and spectroflourometers and the like, having highly diffuse reflectance material mounted along a hollow spherical surface that enables the measurement of diffuse (and specular) reflectance from various sample types and/or transmittance of scattering liquids, films and other specimens.

BACKGROUND

Such light integrating spherical devices have heretofore been used with spectrophotometers and the like, embodying a diffusely reflecting coating, film or layer adhered to the inside of a hollow-spherical surface provided with an appropriate aperture for injecting a light beam for reflection from a holder-held sample exposed at an opposing aperture, or at the center, and/or for transmission through a sample for diffuse reflection transmittance measurements by an appropriate detector monitoring the reflections from the spherical surface, as is well known.

Among the previously used diffuse reflecting coatings, films or layers have been packed or sprayed coatings of barium sulfate, magnesium oxide and/or magnesium carbonate, with a more recently suggested fluorinated aliphatic long chain addition polymer film, alone or coated on a substrate, applied to the inner surface of a hollow sphere, as described in U.S. Pat. Nos. 3,764,364 and 4,035,085. The difficulties with coatings as of barium sulfate and the like reside in sensitivity to moisture and other environmental conditions, degradation with ultraviolet light, relatively low reflectance and efficiency in the ultraviolet and infrared spectra, and mechanical instability in use including under conditions of rough handling, with coating dislodging, and non-susceptibility to cleaning. The problems with the suggested polymer film reside in such mechanical instability and lack of cleanability, also, though, as also recognized in U.S. Pat. No. 4,912,720 of common assignee herewith, improved reflectivity in the ultraviolet and infrared regions can be thereby obtained. The general difficulty of adherence and the different coefficients of expansion and contraction and other environmental responses of coatings or films and the surfaces against which or to which they are applied is also inherent in such prior art integrating spheres.

OBJECTS OF INVENTION

It is, accordingly, an object of the present invention to provide a new and improved integrating sphere primarily for such diffuse reflectance and transmittance use that shall not be subject to such and other disadvantages of prior art coating or film constructions but that, to the contrary, provides mechanical and environmental stability, ready cleanability, and high efficiency throughout the spectrum ranging from the infrared through the visible spectrum and into the ultraviolet region.

A further object is to provide a novel unitary, single-piece block, preferably of fluorinated aliphatic long chain addition polymer and forming method wherein such is hollowed to provide the internal spherical light-reflecting and scattering surface, obviating the need for prior art coatings, films or layering of light diffusing materials.

Other and further objects will be explained hereinafter and are more particularly delineated in the appended claims.

SUMMARY

In summary, however, the invention embraces an integrating sphere for reflectance spectroscopy formed with a block of diffusely reflecting polymeric material internally hollowed into a spherical surface, and provided with aperture means for passing light into the block for one or both of diffuse reflectance and transmittance measurements. Preferred and best mode designs and details are later presented.

DRAWINGS

The invention will now be described in connection with the accompanying drawings, FIG. 1 of which is an isometric view, partly broken away, of the novel integrating sphere of the present invention, illustrating its application to diffuse reflectance measurement;

DESCRIPTION

Figure 1:
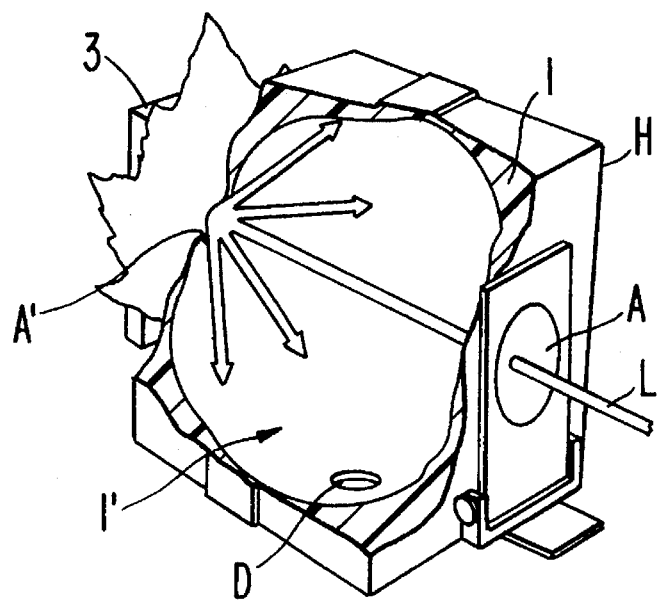

Referring to the drawings, the invention is shown in the form of a single totally enclosed planar-walled hollow cube 1 of said fluorinated long chain aliphatic addition polymer material, sintered into hard block form as described, for example, in said U.S. Pat. No. 4,912,720, and provided with a smooth single-piece unitary inner spherical surface 1'. The block may be formed as joined mating internal hemispherical surfaces, with the hard inner spherical surface machined and/or polished to the desired tolerances.

Figure 3:
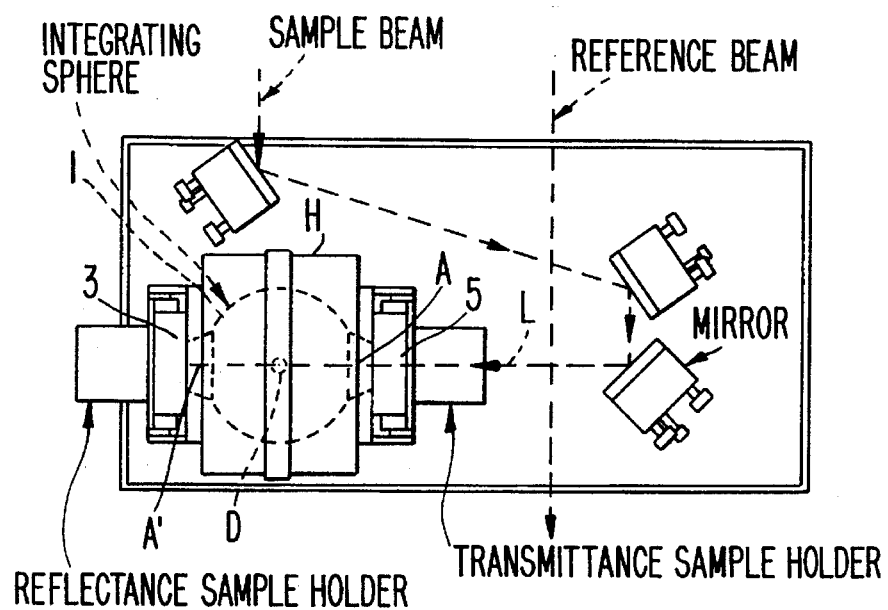
FIG. 3 is a schematic top elevation showing the integrating sphere in use in an optical system of a spectrophotometer, for example.

The integrating sphere block is shown in FIG. 1 as contained in an-outer cubical housing H for mounting as an accessory with a spectrophotometer or similar apparatus, being provided with an aperture A in a planar side wall for receiving the light beam L of such apparatus and passing the same into the into the block as is well known. At the diametrically opposing region, an aperture A' exposes a planar sample holder accessory 3 externally attached for a sample (illustratively shown as a leaf) the diffuse reflectance of which, schematically represented by the arrows, is to be measured at a bottom wall aperature by a conventionally positioned detector D, in customary manner, as described, for example, in said U.S. Pat. Nos. 3,764,364 and 4,035,085, and as shown in FIG. 3.

The preferred fluorinated aliphatic long chain addition polymer material for the block 1 and its integral internal spherical surface 1' is polytetrafluoroethylene (PTFE) having at least one fluorine atom attached to a chain carbon atom; though polychlorotrifluoroethylene, polychlorofluoroethylene, polyvinylidene fluoride and polyvinyl fluoride may be also employed. Through appropriate optical packing density provision and sintering of PTFE, as discussed in said U.S. Pat. No. 4,912,720, an exceptionally high diffuse reflectance characteristic of greater than about 99% can be obtained when the sintered material is formed with void volumes between 30% –50%, with impurity particles less than about 50 microns in diameter, and impurity particle content less than 10 per square inch, and with a pre-sintered density between about 0.8 g/cm$^3$ and 1.5 g/cm$^3$.

Figure 4:
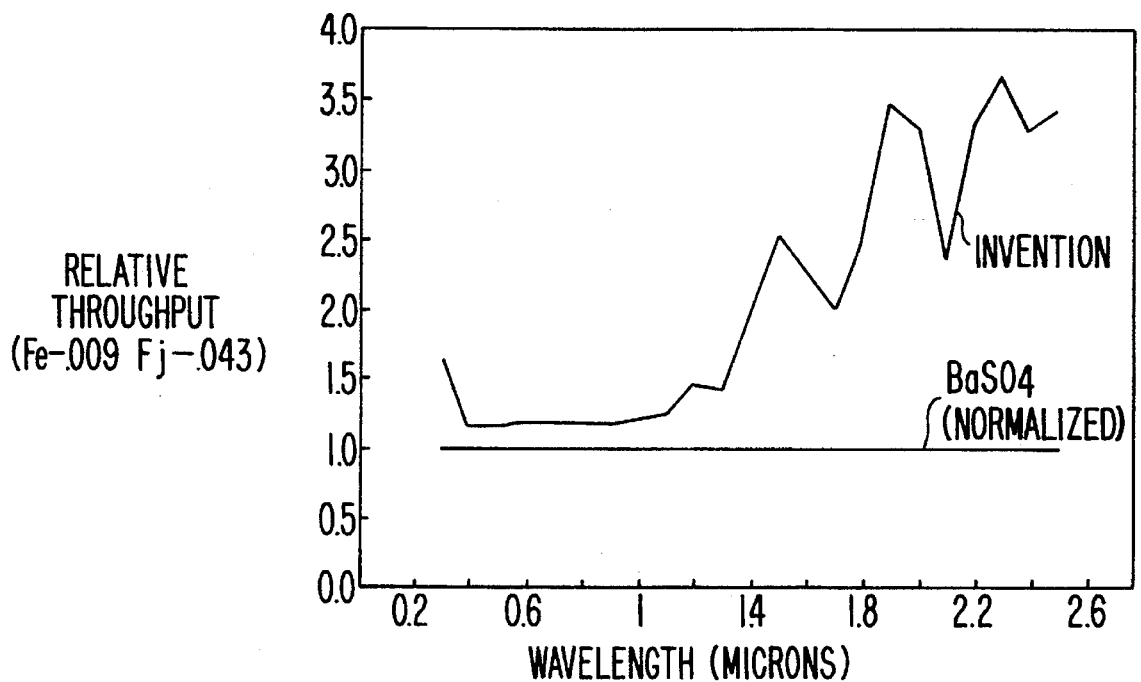
FIG. 4 is a graph contrasting performance with a prior art internally coated sphere.

Referring to the graph of FIG. 4, a comparison is made between the relative throughput of indicent light energy at L reaching the detector at D after reflection and scatter from similar light integrating spherical surfaces—one coated with barium sulfate, and the other, the spherically hollowed PTFE block surface above-described. The factors affecting the signal reaching the detector are certain geometry considerations ($F_e$—the fraction of the sphere covered or monitored by the detector D, and $F_f$—the fraction of the spherical surface taken up by all openings A, A', D) and the reflectance of the spherical wall. For the test represented by FIG. 4, Fe was 0,009 and $F_f$, 0.043, and the barium sulfate data was normalized over the spectrum as shown by the "1.0" horizontal line. The upper curve shows the greater UV efficiency of the invention (0.2 micron range), somewhat better performance over the visible spectrum, and several hundred percent improvement in the near infra red (2.4 micron range).

A typical spherical integrating surface 1' is of the order of 150 mm (6 inches) in diameter, providing a highly diffuse reflectance surface of superior spectral range and extremely stable, reproducable spectral reflectance. This material is durable and maintains consistent reflectance even under harsh laboratory, field or environmental conditions. The total light and detector aperture or port area of the spherical wall is less than about 5%. Extremely accurate reflectance measurements of both diffuse and specular samples is attainable, with the geometry of the spherical surface being diffuse/8° or diffuse/normal, depending on the sample holder used, such being ideal for measuring diffuse reflectance, for example, for scientific and industrial applications including color, thermochromism, composition of opaque materials and biological and geological specimens, among others. The specular reflectance of mirrors and surface reflections from metals or dielectrics, as well as combined diffuse and specular reflectance for glass measurements are all readily measured; and by using variable angle center-mounted sample sample holders, reflectance versus incident radiation angle may be measured. Typical spectrophotometers that can readily employ this accessory include the Perkin-Elmer Lambda 9/19, the Hitachi U-4001, the Hewlett-Packard 8452A, the Milton Roy Spectronic 3000 and the Beckman DU-60 series, among others.

The rugged integral construction of the integrating sphere of the invention, moreover, as contrasted from the above-described coated, film or layered surfaces, is permanent and insensitive to moisture and other environmental conditions and changes, and to de-layering or other disintegration. It is ready cleaned as by separating the hemispherical halves, washing with soap and water, or if necessary, sanding the surface as with sandpaper to restore the surface to its original condition—insuring long life and stable performance even under harsh use conditions that prior art coated spheres have been unable to sustain.

Figure 2:
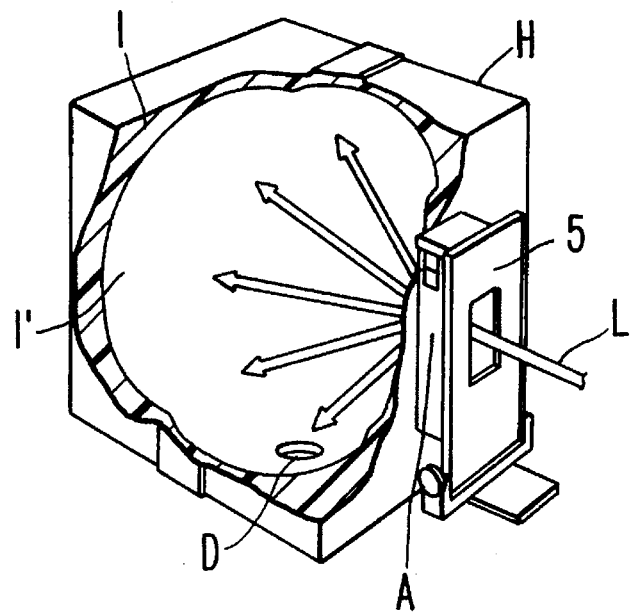
FIG. 2 is a similar view for diffuse transmittance measurement use.

As before stated, the integrating sphere of the invention is also useful for diffuse transmittance, such being shown in FIG. 2 in connection with an externally mounted planar-walled sample holder 5 at the adjacent block planar wall region of the aperture A. Such a system enables the ready measurement of diffuse transmittance of, for example, scattering liquids, translucent films, topical creams and biological and other specimens, as well as performing haze measurements—such being carried out in a normal illumination/diffuse collection geometry, as shown.

Further modifications will also occur to those skilled in this art, such being considered to fall within the spirit and scope of the invention as defined in the appended claims.

What is claimed is:

1. A hollow integrating sphere for reflectance spectroscopy formed within a substantially cubical block of diffusely reflecting hard sintered polymeric material having totally bounding planar external walls internally hollowed into a spherical and polished surface of the said material, and provided in one planar wall thereof with first aperture means for passing an external beam of light into the block, the block externally mounting a sample holder having a planar wall corresponding to the block planar wall at which it is mounted at one of the first aperture means and an oppositely disposed second aperture means for one of diffuse transmittance and reflectance measurements of the sample, and in which the polymeric material comprises at least one fluorinated aliphatic long chain addition polymer having at least one monomer wherein at least one fluorine atom is attached to a chain carbon atom being selected from the group consisting of polytetrafluoroethylene, polychlorotrifluoroethylene, polychlorofluoroethylene, polyvinylidene fluoride and polyvinyl fluoride.

2. An integrating sphere as claimed in claim 1 combined with a sample-measuring spectrophotometer for measuring one of specular and diffuse reflectance and diffuse transmittance of samples and mounted with means for directing a beam of light in the spectrophotometer through the first aperture means, and means for detecting and measuring the light diffusely reflected from the said spherical surface at a third aperture means disposed in the bottom of the block.

3. An integrating sphere as claimed in claim 2 and in which the total aperture area of all aperature means is adjusted to less than about 5% of the spherical surface.

4. An integrating sphere as claimed in claim 2 and in which the spherical surface monitored at the third aperture means by the detecting and measuring means is adjusted to the order of about 0.009.

5. An integrating sphere as claimed in claim 1 and in which the surface is optically polished.

\* \* \* \* \*